United States Patent [19]
Gardner

[11] Patent Number: 5,692,056
[45] Date of Patent: *Nov. 25, 1997

[54] METHOD AND APPARATUS FOR INTRACRANIAL NOISE SUPPRESSION

[76] Inventor: William A. Gardner, 6950 Yount St., Yountville, Calif. 94599

[*] Notice: The term of this patent shall not extend beyond the expiration date of Pat. No. 5,570,426.

[21] Appl. No.: 662,692

[22] Filed: Jun. 13, 1996

Related U.S. Application Data

[63] Continuation-in-part of Ser. No. 35,100, Dec. 7, 1994, Pat. No. 5,570,426.
[51] Int. Cl.⁶ ........................................ A61F 11/06
[52] U.S. Cl. ............................... 381/71.2; 381/72
[58] Field of Search ........................... 381/71, 94, 72, 381/74, 151; 433/27

[56] References Cited

U.S. PATENT DOCUMENTS

| | | |
|---|---|---|
| 4,153,815 | 5/1979 | Chaplin et al. |
| 4,403,176 | 9/1983 | Cranston |
| 5,133,017 | 7/1992 | Cain et al. |
| 5,140,640 | 8/1992 | Graupe et al. |
| 5,226,016 | 7/1993 | Christman |
| 5,278,913 | 1/1994 | Delfosse et al. |
| 5,295,192 | 3/1994 | Hamada et al. |
| 5,305,387 | 4/1994 | Sapiejewski |
| 5,313,945 | 5/1994 | Friedlander |
| 5,418,858 | 5/1995 | Shoureshi |
| 5,427,102 | 6/1995 | Shimode et al. |
| 5,570,426 | 10/1996 | Gardner .................. 381/71 |

*Primary Examiner*—Curtis Kuntz
*Assistant Examiner*—Ping W. Lee
*Attorney, Agent, or Firm*—John P. O'Banion

[57] ABSTRACT

A method and apparatus for active cancellation of vibrational noise produced by a medical instrument in the head of a patient. Vibrations from the instrument, as well as vibrations in the bone structure in the head of the patient, are sensed and processed to generate cancelling noise waves which are then fed into the inner ear through vibrators placed on the head of the patient. An equalizer shapes the magnitude and phase spectrum of the vibrational signal picked up from the drill and delivers the equalized vibrational signals to the patient. An automatic adaptive controller adjusts the equalizer using control signals consisting of vibrations from the bone structure and the drill.

9 Claims, 3 Drawing Sheets

METHOD AND APPARATUS FOR INTRACRANIAL NOISE SUPPRESSION

CROSS-REFERENCE TO RELATED APPLICATIONS

This application is a continuation-in-part of U.S. application Ser. No. 08/351,005, dated Dec. 7, 1994, now U.S. Pat. No. 5,570,426, which is incorporated by reference herein.

BACKGROUND OF THE INVENTION

1. Field of the Invention

This invention pertains generally to noise cancellation methods and devices, and more particularly to a method and apparatus for actively suppressing noise vibrations transmitted from a medical instrument through bone structure and intracranial tissue in the head.

2. Description of the Background Art

In 1844, when Horace Wells introduced anesthesia, including nitrous oxide, and later in 1896 when sulfuric ether was introduced, the discomfort experienced by patients receiving dental health care sharply declined. Today, general anesthesia is considered dentistry's greatest discovery. However, in 1872 when S. S. White Company introduced the first electric drill which was invented by George F. Green, the discomfort caused by drill noise began to increase and continued to do so with further increases in drill speed. The level of discomfort reached a maximum for many patients when the high-speed pneumatic turbine drills were introduced in the 1960's. Today, dentists report that the chief complaint they receive from their patients is-aside from the hypodermic needle—the discomfort from noise caused by either the high-frequency whine of the high-speed (300, 000–400,000 maximum RPM) drills or, for some, the chatter and vibration of the so-called low-speed (around 30,000 maximum RPM) drills.

Some reduction of perceived drill noise can be accomplished by muffling the patient's ears, or by using "active headsets" which both muffle the patient's ears and perform noise cancellation of the sound which propagates through the air to the patient's ears. However, even with total suppression of the pressure waves arriving at the ear due to drill noise propagating through the air, dental patients experience only negligible reduction in discomfort because a great deal of the drill noise perceived arrives at the inner ear from propagation paths through the head. That is, the vibration induced in the tooth by the drill enters the bone and propagates along the skull and through the skull interior to the temporal bone and finally to the inner, middle, and outer ears, each of which contributes to the vibrations in the cochlea which are converted to nerve impulses that are sent on to the brain.

Vibrational energy can travel along two different pathways to the cochlea: through the bone, and through the skull interior. Energy transmitted by these pathways is brought together at the temporal bone. From that point, there is a signal line that goes to three separate points of input: (1) the walls of the external auditory canal, (2) the middle ear ossicle, and (3) the cochlear capsule and its contained fluid. In addition, the cochlea has an independent input from the skull interior via what is referred to as the "third window". At each of these points, which represent separate inputs to the outer, middle, and inner ears, respectively, the responses are altered by a number of modifying factors. Specifically, the walls of the external canal radiate sound into its lumen (air), the modifying fact being the external opening, acting as a high-pass filter. The middle ear ossicles respond because of their moment of inertia, this response being modified by the tympanic membrane and the air enclosed in the middle ear, both acting like backsprings. The cochlear capsule undergoes distortional vibrations. The mass of the contained fluid, being unequally distributed, responds in an inertial manner. This cochlear response is modified by the oval and round windows which have not only different compliance values of their own, but face different impedances in the middle ear: the oval window, the ossicular chain; the round window, and the air enclosed in the middle ear.

Finally, along what might be called response line, i.e., the air in the external canal, the tympanic membrane, the ossicular chain, the oval window, and the cochlea, all of these various responses are collected and integrated with one another, according to their phase relationships, and the integrated response finally leads to hair cell stimulation, which creates the nerve impulses that go on to the brain via the auditory nerve.

Some researchers have previously demonstrated that a tone introduced simultaneously into the auditory canal and the skull (using a vibrator pressed against the head), with relative phase and magnitude adjusted properly, would result in no perception of sound in one or the other ear. However, there does not appear to have been any studies of the cancellation of more complex vibrational patterns inside the head. Some researchers have also demonstrated that some degree of reduction in structural vibration can be accomplished through active cancellation techniques. However, no such work on human structures has been found, and prior techniques require access to regions in which zonal nulls are desired.

Therefore, a need exists for a method and apparatus for nulling vibrational noise propagating through the bone structures and intracranial tissue in the head to the inner ear, and more particularly for a method and apparatus which will cancel vibrational noise in the inner ear zones transmitted to a patient from a medical instrument. The present invention satisfies that need, as well as others, and overcomes the deficiencies in prior methods and devices.

SUMMARY OF THE INVENTION

The present invention pertains generally to reducing the discomfort of a patient and the associated exacerbation of perceived pain by suppressing the vibrations propagating through the bone structure and intracranial tissue of the head from a medical instrument using active vibration cancellation and, more particularly, to hulling the vibration waveforms in the inner ear by zonal nulling that results from superposition of electronically processed waveforms with appropriate magnitude and phase relationships. The invention can be used to suppress vibrational noise generated by dental drills, as well as bone cutting tools used in brain and mastoid surgery.

In particular, the present invention improves upon the method and apparatus for intracranial noise suppression described in my co-pending application Ser. No. 08/351,004 by improving the adaptation of equalizers whose A/D-converted outputs drive head worn vibrators to cancel drill-induced vibration at the inner ear. One aspect of the present invention pertains to the removal of manually adjusted equalizers during adaptation and subsequent reinsertion after adaptation. Another aspect of the present invention also pertains to the capability of an embodiment of the new invention to seek only to suppress the tonal component in the drill-induced vibration at the inner ear, which component may be perceived by the patient as the most annoying portion of the drill-induced vibration.

By way of example, and not of limitation, vibrations from the medical instrument, as well as vibrations in the bone structure in the head of the patient, are sensed by accelerometers and processed to generate cancelling noise waves which are then transmitted to the inner ear through vibrators placed on the head of the patient. An equalizer contained in a digital signal processing (DSP) chip shapes the magnitude and phase spectrum of the vibrational signal picked up from the medical instrument and delivers the equalized signal to the patient. An adaptive controller, also contained in the DSP chip, automatically adapts and adjusts the equalizer using control signals consisting of vibrations from the bone structure and the medical instrument.

An object of the invention is to provide for wave superposition inside the subject's head that results in zonal nulls in the two regions containing the left and right inner ears where sound is converted into nerve impulses.

Another object of the invention is to provide for vibration cancellation at the inner ears, which are regions of the body that are inaccessible for the placement of sensors that monitor the degree of suppression.

Another object of the invention is to provide for vibration cancellation using wave-input devices and wave pick-up devices that are comfortable, convenient, and otherwise acceptable by both the dentist or surgeon and the patient.

Another object of the invention is to provide a vibration cancelling method and apparatus that is adaptable to the variety of head characteristics, such as head size and shape and thickness and density of tissue covering bone.

Another object of the invention is to provide for a vibration cancelling method and apparatus that can adapt to the rapidly changing magnitude and phase characteristics of the interface between the medical instrument and the head due to intentional motion of the medical instrument and inadvertent vibration and chatter between the medical instrument and the head.

Further objects and advantages of the invention will be brought out in the following portions of the specification, wherein the detailed description is for the purpose of fully disclosing preferred embodiments of the invention without placing limitations thereon.

BRIEF DESCRIPTION OF THE DRAWINGS

The invention will be more fully understood by reference to the following drawings which are for illustrative purposes only.

DESCRIPTION OF THE PREFERRED EMBODIMENTS

Figure 1:
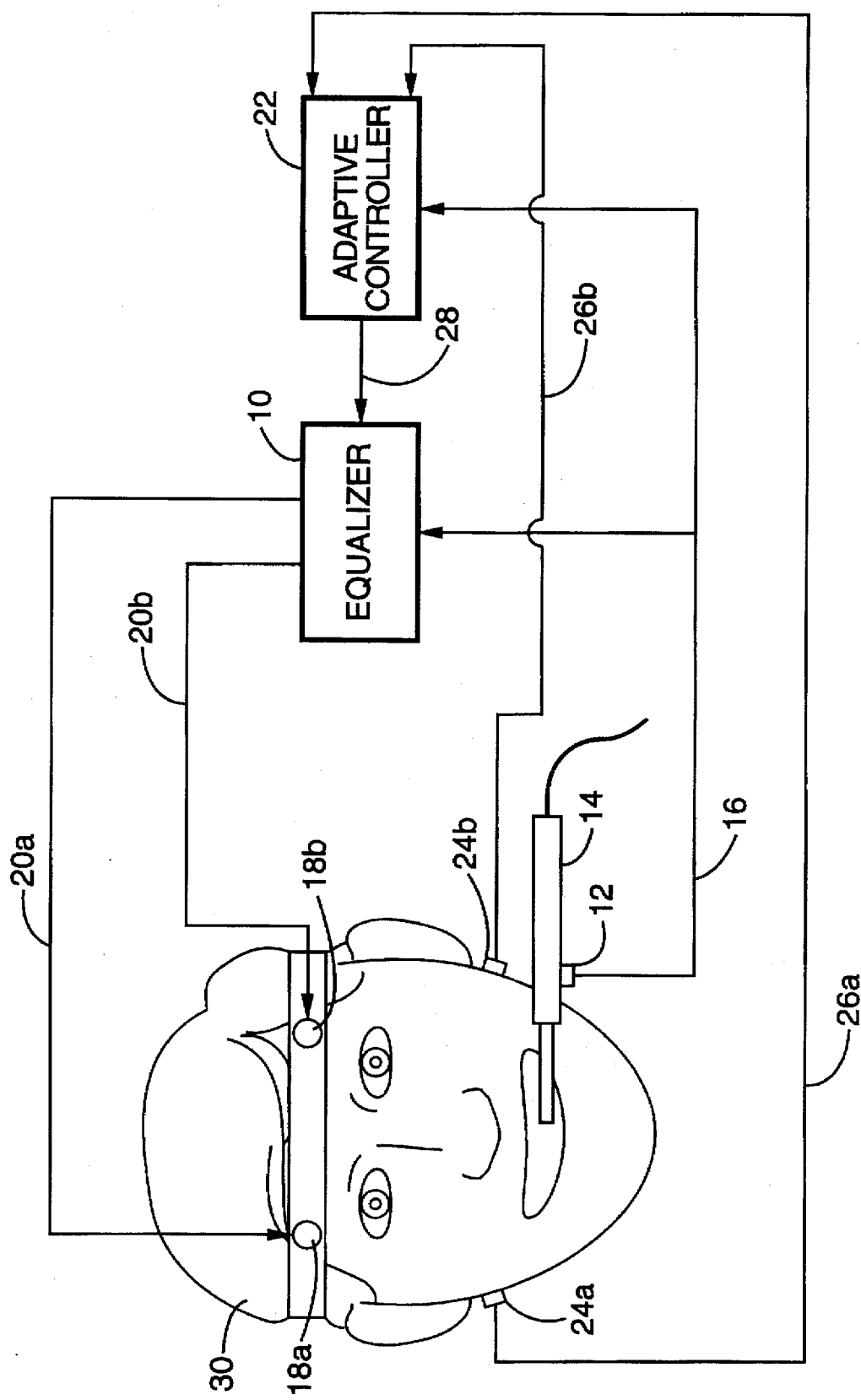
FIG. 1 is system diagram showing the apparatus of the present invention coupled to a human user and a medical instrument.
Figure 2:
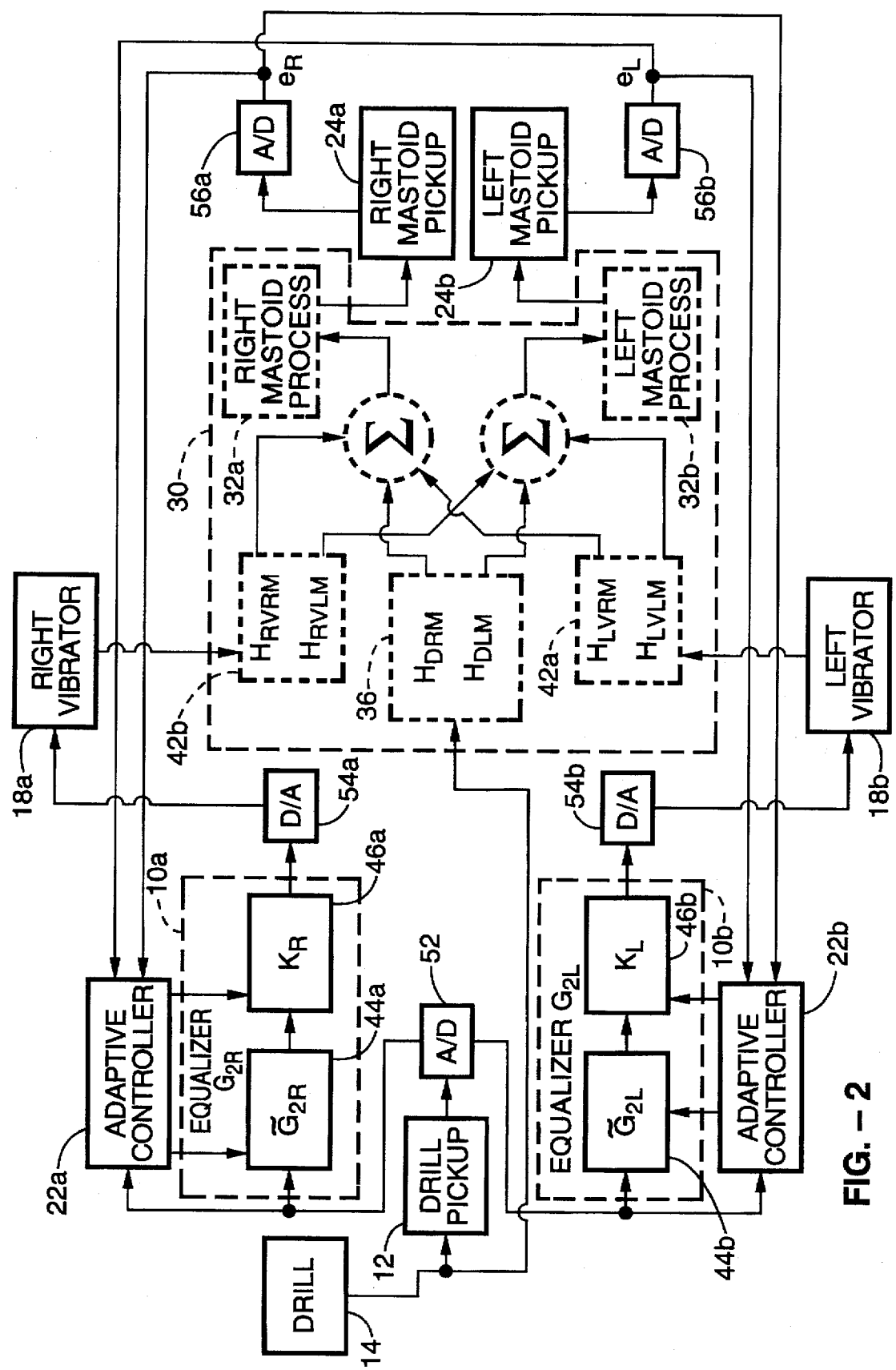
FIG. 2 is a functional block diagram showing the equalizer adaptation process of the apparatus shown in FIG. 1.
Figure 3:
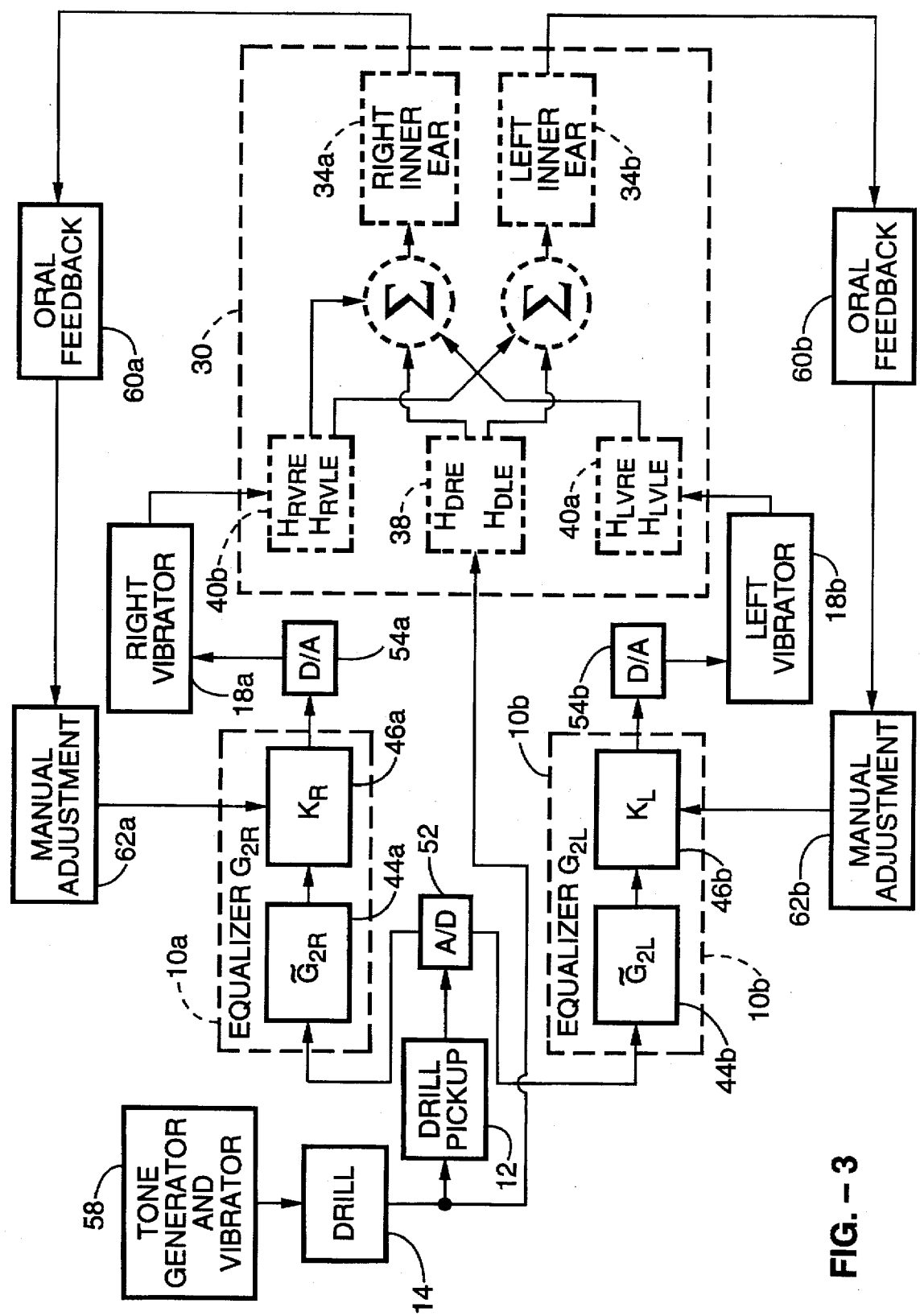
FIG. 3 is a functional block diagram showing the equalizer calibration process of the apparatus shown in FIG. 1.

Referring more specifically to the drawings, for illustrative purposes the present invention is embodied in the intracranial noise suppression apparatus and method generally shown in FIG. 1 through FIG. 3, as more fully described herein, where like reference numerals denote like parts. It will be appreciated that the apparatus may vary as to configuration and as to details of the parts, and that the method may vary as to the steps and their sequence, without departing from the basic concepts as disclosed herein. It will further be appreciated that, while the drawings depict a dental drill as the source of vibrational noise, the invention can be used with bone cutting tools in connection with brain or mastoid surgery, as well as with other medical instruments which generate intracranial vibrations.

Referring to FIG. 1, the invention includes an equalizer 10 which is electrically connected to a drill vibration pickup 12, such as a conventional accelerometer or like vibration sensor, which is in turn mechanically coupled to a drill 14. Equalizer 10, the input of which is connected to drill vibration pickup 12 through interconnection 16, shapes the magnitude and phase spectrum of the vibration signal picked up from drill 14 and delivers equalized output signals to a right head-worn vibrator 18a and a left head-worn vibrator 18b, to which it is electrically connected through interconnections 20a and 20b, respectively. The invention also includes an adaptive controller 22 which has an input electrically connected to drill vibration pickup 12 through interconnection 16, and inputs electrically connected to right 24a and left 24b mastoid pickups through interconnections 26a and 26b, respectively. Right 24a and left 24b mastoid pickups are conventional accelerometers or like vibration sensors similar to drill vibration pickup 12. Adaptive controller 22, the output of which is connected to an input of equalizer 10 through interconnection 28, adaptively adjusts equalizer 10 using the vibration signals from drill vibration pickup 12, and right 24a and left 24b mastoid pickups. The adaptively equalized vibrations emanating from the right 18a and left 18b head-worn vibrators are physically introduced into the patient 30 and cause vibrations in the inner ear. The vibration sensors and vibrators are configured for coupling to the drill and the patient, as indicated above, using conventional coupling means.

Referring to FIG. 2 and FIG. 3, the method and apparatus of the invention can be seen in more detail. The relevant model of drill-induced vibration in the head consists of four parallel channels with transfer functions denoted by H(f), a function of frequency f. These channels are: the channel from drill 14 to the right mastoid process 32a ($H_{DRM}$), the channel from drill 14 to the left mastoid process 32b ($H_{DLM}$), the channel from drill 14 to the right inner ear 34a ($H_{DRE}$), and the channel from drill 14 to the left inner ear 34b ($H_{DLE}$), where $H_{DRM}$ and $H_{DLM}$ are the transfer functions for the physical channels inside the head from the drill to the right 32a and left 32b mastoid processes, respectively, multiplied by the transfer function for the mastoid pickup, and are shown as element 36 in FIG. 2; and where $H_{DRE}$ and $H_{DLE}$ are the transfer functions for the physical channels inside the head from drill 14 to the right 34a and left 34b inner ears, respectively, and are shown as element 38 in FIG. 3. Note that, for simplicity, H(f) has been abbreviated to H.

There are eight channels in the relevant model of vibrator-induced vibration in the head: the channel from the right vibrator 18a to the right inner ear 34a ($H_{RVRE}$), the channel from the right vibrator 18a to the left inner ear 34b ($H_{RVLE}$), the channel from the right vibrator 18a to the right mastoid process 32a ($H_{RVRM}$), the channel from the right vibrator 18a to the left mastoid process 32b ($H_{RVLM}$), the channel from the left vibrator 18b to the right inner ear 34a ($H_{LVRE}$), the channel from the left vibrator 18b to the left inner ear 34b ($H_{LVLE}$), the channel from the left vibrator 18b to the right mastoid process 32a ($H_{LVRM}$), and the channel from the left vibrator 18b to the left mastoid process 32b ($H_{LVLM}$), where $H_{LVRE}$, $H_{LVLE}$, $H_{RVLE}$, and $H_{RVRE}$ are the transfer functions from the vibrator location on the skin or tooth through the head to the inner ear times the transfer function for the vibrator, and where $H_{LVRM}$, $H_{LVLM}$, $H_{RVLM}$, and $H_{RVRM}$ are the transfer functions from the vibrator location to be mastoid process times the transfer function for the vibrator times the transfer function for the mastoid pickup. $H_{LVRE}$ and $H_{LVLE}$ are shown as element 40a, $H_{RVLE}$ and $H_{RVRE}$ shown as element 40b, $H_{LVRM}$ and $H_{LVLM}$ are shown as element 42a, and $H_{RVLM}$ and $H_{RVRM}$ are shown as element 42b.

Separating the chapels in equalizer 10 so as to denote the equalizers for the right 34a and left 34b ears as $G_{2R}$ and $G_{2L}$, respectively, which are shown as elements 10a and 10b, the conditions on the equalizers for a null at the right and left ears are, respectively, $$G_{2R}H_{RVRE}+G_{2L}H_{LVRE}=-H_{DRE} \qquad (1)$$

$$G_{2L}H_{LVLE}+G_{2R}H_{RVLE}=-H_{DLE} \qquad (2)$$

On the other hand, if we adapt the equalizers 10a, 10b for nulls at the two plasmid processes 32a, 32b then we satisy the following conditions:

$$\tilde{G}_{2R}H_{RVRM}+\tilde{G}_{2L}H_{LVRM}=-H_{DRM} \qquad (3)$$

$$\tilde{G}_{2L}H_{LVLM}+\tilde{G}_{2R}H_{RVLM}=-H_{DLM} \qquad (4)$$

where the notation $\tilde{G}$ indicates that the solution m equations (3) and (4) differs from the solution G to equations (1) and (2). Let us define the following 2×2 matrices and 2×1 vectors:

$$H_{VE} = \begin{bmatrix} H_{RVRE} & H_{LVRE} \\ H_{RVLE} & H_{LVLE} \end{bmatrix} \qquad (5)$$

$$H_{VM} = \begin{bmatrix} H_{RVRM} & H_{LVRM} \\ H_{RVLM} & H_{LVLM} \end{bmatrix} \qquad (6)$$

$$H_{DE} = \begin{bmatrix} -H_{DRE} \\ -H_{DLE} \end{bmatrix} \qquad (7)$$

$$H_{DM} = \begin{bmatrix} -H_{DRM} \\ -H_{DLM} \end{bmatrix} \qquad (8)$$

$$G_2 = \begin{bmatrix} G_{2R} \\ G_{2L} \end{bmatrix} \qquad (9)$$

$$\tilde{G}_2 = \begin{bmatrix} \tilde{G}_{2R} \\ \tilde{G}_{2L} \end{bmatrix} \qquad (10)$$

Then we can write the solutions to equations (1) through (4) as $$G_2 = H_{VE}^{-1} H_{DE} \text{ and} \qquad (11)$$

$$\tilde{G}_2 = H_{VM}^{-1} H_{DM} \qquad (12)$$

Let us now define two transfer functions to be the ratios of elements of the vectors in equations (11) and (12):

$$K_R = G_{2R}/\tilde{G}_{2R} \qquad (13)$$

$$K_L = G_{2L}/\tilde{G}_{2L} \qquad (14)$$

If we adapt the equalizers 10a, 10b to produce nulls at the two mastoid processes 32a, 32b, we get the solution given by equation (12). But, if we put in series with each of these equalizers a corrective equalizer with transfer functions given by (13) and (14), we obtain the composite equalizers $$G_{2R} = \tilde{G}_{2R} K_R \qquad (15)$$

$$G_{2L} = \tilde{G}_{2L} K_L \qquad (16)$$

which satisfy equation (11) and therefore produce nulls at the two inner ears 34a, 34b.

It should be noted that, neither the mastoid pickup nor any other conceivable and practical pickup can sense directly a null at the inner ear, implying that the right side of equation (11) cannot be measured. This motivates the use of equation (12). Note also that equations (13)–(14) specify conditions for nulls at the inner ears, not an algorithm for finding $K_R$ and $K_L$ (since $G_2$ is not known). $K_R$ and $K_L$ must be determined through manual adjustment.

Let us now consider how the equalizers $\tilde{G}_2$ are adapted using the differential equalizers $$K = \begin{bmatrix} K_R \\ K_L \end{bmatrix} \qquad (17)$$

to satisfy the preceding equations. The vibrations reaching the two inner ears from the tooth being drilled are cancelled in zones containing the two inner ears by the superposition of the vibrations picked up from the drill casing, and fed through two jointly adapted equalizers to a pair of vibrators. Each equalizer is part of a parallel channel from the drill casing, through the pickup, the equalizer, the vibrator and the head, to the inner ear. The adaptation minimizes the residual (uncancelled) drill noise appearing nearby the inner ears (at the mastoid processes). Assuming that the mismatch between the channels to the inner ears and the parallel channels to the nearby mastoids leaves an unacceptably large residual at the inner ears (when nulls are achieved at the mastoid processes), manually adjustable equalizers $K_R$ and $K_L$ are inserted in series with each of the two automatically adaptive equalizers $\tilde{G}_2$. These differential equalizers, collectively referred to as K, compensate for the difference between channels to each inner ear and each mastoid process.

The adaptation method comprises determining $K_R$ and $K_L$ through an initial manual adjustment process, and running an LMS, RLS (recursive least squares), or other type of algorithm to periodically and jointly update the equalizers $\tilde{G}_{2R}$ and $\tilde{G}_{2L}$, which are denoted as elements 44a, 44b in series with $K_R$ and $K_L$, which are denoted as elements 46a, 46b. Although it would appear to be desirable to adapt $\tilde{G}_{2R}$ and $\tilde{G}_{2L}$ without interruption, this is not desirable because $K_R$ and $K_{2L}$ must be removed from the equalizers $G_{2R}$ and $G_{2L}$ during adaptation in order for $\tilde{G}_{2R}$ and $\tilde{G}_{2L}$ to adapt in the most desirable manner, and then $K_R$ and $K_L$ must be reinserted in order for the overall equalizers $G_{2R}$ and $G_{2L}$ to produce the deepest nulls at the inner ears. In order for the patient to perceive continuous hulling when, in fact, nulls are absent periodically (during adaptation when $K_R$ and $K_L$ are removed) the adaptation periods must be sufficiently short. This calls for particularly rapid adaptation using, for example, the RLS algorithm or a computationally efficient modification thereof, such as the fast affine projection algorithm (which is described in the literature on noise cancellation). Nevertheless, the LMS algorithm, which is the most computationally efficient, might converge rapidly enough.

The aforementioned removal and insertion of $K_R$ and $K_L$ is controlled by adaptive controllers 22a, 22b. Equivalently, the desired effect of removal can be obtained by the adaptive controllers by saving the coefficient values of $K_R$ and $K_L$ to the internal memory of the controllers and replacing $K_R=K_L=1$. The reinsertion can then be accomplished by restoring the saved coefficient values from the internal memory of the controllers.

Although the LMS algorithm can jointly adapt the two (left and right) equalizers, as needed to accommodate cross coupling between left (right) vibrator and right (left) inner ear (and mastoid), this need for joint adjustment complicates the manual adjustment procedure.

Note also, that the analog output of drill vibration pickup 12 is processed by an analog to digital convertor (A/D) 52 with the digital output thereof being fed into right 10a and left 10b equalizers and right 22a and left 22b adaptive controllers, that the digital outputs of right 10a and left 10b equalizers are processed by right 54a and left 54b digital to analog convertors (D/A) with the analog outputs thereof being fed to right 18a and left 18b head-worn vibrators, respectively, and that the analog outputs of right 24a and left 24b mastoid pickups are processed by right 56a and left 56b analog to digital convertors with the digital outputs thereof being fed into right 22a and left 22b adaptive controllers, respectively. These A/D and D/A convertors are of a conventional type.

To describe the LMS-type of adaptation algorithm, let $x(n)$ denote the digital input to the equalizer 10. The outputs of the automatically adjustable portion of the two equalizers $G_{2R}$ and $G_{2L}$ are $$y_m(n) = \sum_{i=0}^{N-1} w_{mi}(n)x(n-i), \, m=1,2 \tag{18}$$

where $w_{1i}(n)$ and $w_{2i}(n)$ are the time-dependent (due to adaptation) impulse responses of $\tilde{G}_{2R}$ and $\tilde{G}_{2L}$, respectively. The digitized error signals at the outputs of the right and left mastoid pickups are $e_R(n)=e_1(n)$ and $e_L(n)=e_2(n)$, respectively. The multiple-error filtered-data (MEFD) LMS algorithm (without gradient deflection) can then be expressed as $$w_{mi}(n+1) = w_{mi}(n) - a \sum_{q=1}^{2} e_q(n)r_{qm}(n-i) \tag{19}$$

for $m=1, 2$ and $i=0, 1, 2, \ldots, N-1$, where $a$ is a step-size parameter, and $r_{qm}(n)$ is the filtered data $$r_{qm}(n) = \sum_{j=0}^{J-1} c_{qmj}x(n-j) \tag{20}$$

where $c_{qmj}$ is the j-th element of the impulse response of the series connection of the drill pickup 12, A/D converter 52, right 46a ($K_R$) or left 46b ($K_L$) manually adjustable differential equalizer, right 54a or left 54b D/A convertor, right 18a or left 18b vibrator, and the internal head channel of patient 30, according to the channel of interest. The corresponding transfer functions are $$C_{11}=K_R V_R H_{RVRM} \tag{21}$$

$$C_{12}=K_R V_R H_{RVLM} \tag{22}$$

$$C_{21}K_L V_L H_{LVRM} \tag{23}$$

$$C_{22}K_L V_L H_{LVLM} \tag{24}$$

where $V_R$ and $V_L$ are the transfer functions of the digital to analog convertors. The corresponding four impulse responses for equations (21) through (24) need to be estimated prior to initiation of the MEFD-LMS algorithm. This can be done by using the transfer-function formulas $$C_{11}=E_R/X \tag{25}$$

$$C_{12}=E_L/X \tag{26}$$

with the drill 14 and left vibrator 18b turned off, and $x(n)$ equal to the output from the right vibrator 18a and A/D convertor 52, and $$C_{21}=E_R/X \tag{27}$$

$$C_{22}=E_L/X \tag{28}$$

with the drill 14 and right vibrator 18a turned off, and $x(n)$ equal to the output from the left vibrator 18b and A/D convertor 52. $E_R$, $E_L$, and $X$ are the complex spectra of $e_R(n)$, $e_L(n)$, and $x(n)$.

The step size $a$ should not exceed $$a_{max} = \frac{1}{(<r_{1m}^2> + <r_{2m}^2>)(N+D)} \tag{29}$$

where D is the overall delay from right 54a or left 54b D/A convertor through right 18a or left 18b vibrator to the opposite mastoid pickup.

Since the MEFD-LMS algorithm is well known, a detailed description thereof is not presented herein.

Referring also to FIG. 3, the manual adjustment procedure for $K_R$ and $K_L$ must be preceded by an initial adaptation of the equalizers $\tilde{G}_{2R}$ and $\tilde{G}_{2L}$ to produce nulls at the two mastoid processes. For initial adaptation, $K_R=K_L=1$, and the transfer functions of equations (21) through (24) must be measured. This can be done by applying a vibrational test signal to the tooth to be drilled via tone generator/vibrator 58 attached to the drill 14 with the drill casing pressed against the tooth, prerecorded drill noise, or another form of test signal that consists of the simultaneous presence of all tones to be nulled during the manual adjustment phase. After the adaptive equalizer $\tilde{G}_2$ has converged (e.g., 1 second after application of the test signal), the patient 30, or a dentist or dental assistant with oral feedback 60a, 60b from the patient 30, can adjust the magnitude and phase of the differential equalizers K (or a model thereof) using a right 62a and left 62b two-dimensional control until the equalized signal passing through the two-preadapted equalizers 44a, 44b, the two vibrators 18a, 18b, and the two differential equalizers 46a, 46b, nulls (at the inner ear) the test signal fed through the tooth to be drilled. In this regard, note that the null is a perceptual null as sensed by the patient in each ear. This is done for each of a set of tones strategically placed throughout the spectral band of the drill noise. This two-dimensional control could be, for example, a lever attached to a ball in a socket (a "joy stick"), or it could be, as other examples, an x-y coordinate control, or a track ball. The two dimensions in which control takes place represent the magnitude and phase of the equalizer at the tone frequency. Or, as an alternative, the magnitude and phase can be automatically swept through the desired range and the patient can push a button when a null is sensed. If a finite impulse response (FIR) structure is used for the equalizer, then this magnitude and phase can be implemented separately, and when the entire set of magnitudes and phases have been determined they can be fit to a transfer function and inverse Fourier transformed to produce the desired FIR impulse response.

The manual adjustment phase may take as long as 5 minutes, but can be carried out while waiting for the anesthesia to take effect.

Once differential equalizers 46a, 46b have been adjusted, they need no further adjustment (during drilling) because the differential channel should undergo only negligible change during drilling (provided that the mastoid pickup is physically stationary relative to the inner ear).

After the manual adjustment has been completed, the previously measured transfer functions can be modified as in equations (21)–(24) by multiplication with $K_R$ and $K_L$. Otherwise, they can just be remeasured. Since the accuracy of these measurements is not especially important, the easiest of these two methods to implement should be used. The two transfer functions K determined by the magnitudes and phases learned during manual adjustment can be transformed to two equivalent impulse responses, which can then be implemented as FIR filters. Similarly, the adaptive equalizers $\tilde{G}_2$ can be implemented as FIR filters so that they can be adapted with a least mean square (LMS) type of algorithm, possibly with a convergence-accelerating gradient-deflecting matrix precomputed from typical drill noise or, possibly, adapted during drilling. Note, however, that this gradient deflection might speed up overall convergence but might slow down the suppression of the tonal components of the noise, which might be the most annoying part of the drill noise.

An alternative embodiment of the present invention seeks only to suppress the dominant tonal or, more accurately, narrowband component, rather than the totality, of the drill-induced vibration at the inner ear. Such an alternative embodiment can be substantially similar to the preferred embodiment depicted in FIG. 1 through FIG. 3, with the exceptions being that means for estimating the time-varying center frequency $f_c$ of the dominant narrowband component are provided (e.g., incorporated into the adaptive controllers 22a, 22b) and means for constraining the adaptive equalizers $\tilde{G}_{2R}$ and $\tilde{G}_{2L}$ to attenuate substantially all input outside the narrow spectral band centered at the estimate of the center frequency $f_c$.

The estimation of the center frequency $f_c$ must be performed frequently enough to track the changes in $f_c$ due to changes in drill speed. Those skilled in the art will appreciate that the estimation of $f_c$ can be implemented in any of several ways, including but not limited to, finding the location of the peak in the sliding windowed fast Fourier transform (FFT) of the signal within the candidate frequency band from the drill pickup, or finding the first moment (center of mass) of this FFT, or indirectly by fitting an autoregressive (AR) linear model to the data. The candidate frequency band depends on the rotational speed of the drill and can be constrained by previous estimates of $f_c$ (e.g., to prevent unreliable and erratic fluctuations). For example, for high-speed drills (200,000 to 400,000 RPM), the candidate frequency band is approximately 3500 Hz to 6500 Hz, possibly constrained further to lie in the intersection between this band and the band centered at the previous estimate of $f_c$ and having a width of 2000 Hz. Those skilled in the art will appreciate that alternate means of constraining estimates may be employed including, but not limited to, simply smoothing the sequence of estimates or more generally through the use of Kalman filtering.

The adaptive equalizers $\tilde{G}_{2R}$ and $\tilde{G}_{2L}$ may be constrained to attenuate substantially all input outside the narrow spectral band centered at the estimate of $f_c$ in many ways including, but not limited to, conventional subband filtering techniques.

While the embodiment of FIG. 1 through FIG. 3 uses vibrators placed on the forehead of the patient, other useful input locations for the cancelling noise were found to include teeth other than those being drilled (this is for convenience of the dentist, because the tooth being drilled is also a useful input location for the cancelling vibration), the two mastoid processes, the two temporal bones, the two cheek bones, and the jaw bone, although the jaw bone yielded the weakest sensation at the ear because of the joint between the jaw and the skull. In other words, just about anywhere on the head that bone is close to the skin was found to be a useful location. This is understandable since the dimensions of the head are comparable with the wavelengths in the drill vibration. Nevertheless, the most effective location, in terms of perceived volume of vibration induced on the exterior of the head, was found to be the mastoid processes and the sides of the forehead just in front of the temples. If the mastoid location is used for vibration pick up as in FIG. 1 through FIG. 3, however, this leaves the forehead locations open for the vibrators.

The teeth are especially attractive locations for the vibrators, because of their proximity to the source of the drill noise to be suppressed. This results in the largest extent of the zone in which nulling occurs. However, because of the possible bulkiness of sufficiently powerful vibrators, it might be too inconvenient for the dentist and patient to apply these to teeth. If small vibrators with convenient means for attachment to the upper back teeth is deemed possible, this would seem to be the best location from a noise suppression standpoint. Otherwise, the sides of the forehead, just in front of the temple as shown in FIG. 1 seems to be the next best place in terms of providing good coupling to inner ears with minimal delay, minimal cross coupling (left vibrator to right ear), and sufficient distance from error pickups at mastoids.

With regard to the location of the vibration pick-ups, the best position was found to be that which is closest to the inner ear, with good coupling from the bone surrounding the inner ear; that is, the left and right mastoid processes. Note, however, that the location for these noise-suppression-error pickups are each about one inch from each of the inner ears, and the wavelengths of vibration in the skull range from a minimum of about two inches at the highest frequencies of interest. Therefore, the correspondence between nulls at the inner ear and the mastoid process might not be precise enough to adequately null out the higher frequencies. This potential problem is accommodated as described above. The best impedance matching between skin and pickup can be obtained by using a putty between the pickup and the skin covering the mastoid.

Those skilled in the art will appreciate that the present invention can be implemented using standard analog electronic circuitry or, more economically, standard digital circuitry, including microcomputers. The equalizer 10 and adaptive controller 22 can reside, for example, on a digital signal processor (DSP) chip such as a Texas Instruments TMS320C31 or equivalent. The DSP chip, A/D convertors, D/A converters, and related input/output circuitry are conventional, and can be fabricated on a single DSP board.

Accordingly, it will be seen that this invention provides a method and apparatus for actively cancelling vibrational noise produced by a medical instrument, thereby relieving discomfort and associated exacerbation of perceived pain. Although the description above contains many specificities, these should not be construed as limiting the scope of the invention but as merely providing illustrations of some of the presently preferred embodiments of this invention. Thus the scope of this invention should be determined by the appended claims and their legal equivalents.

What is claimed is:

1. An apparatus for intracranial noise suppression, comprising:
   (a) mechanical vibration sensing means for sensing mechanical vibration signals generated by a medical instrument;
   (b) intracranial vibration sensing means, configured for attachment to a patient's head, for sensing intracranial vibration signals induced by said medical instrument in the patient;
   (c) equalizing means for processing said mechanical and intracranial vibration signals and generating equalizing vibration signals which suppress said intracranial vibration signals;
   (d) adaptive controller means for adapting said equalizing means to changes in said mechanical and intracranial vibration signals; and
   (e) vibration transmitting means for transmitting said equalizing vibration signals to said patient.

2. An apparatus as recited in claim 1, further comprising means for calibrating said equalizing means.

3. An apparatus as recited in claim 1, wherein said mechanical vibration sensing means and said intracranial vibration sensing means comprise accelerometers.

4. An apparatus as recited in claim 1, wherein said transducing means comprises a vibrator.

5. An apparatus for suppressing intracranial noise generated by a medical instrument, comprising:
   (a) a first accelerometer, said first accelerometer configured for coupling to a medical instrument;
   (b) second and third accelerometers, said second and third accelerometers configured for coupling to a corresponding one of said patient's left and right mastoid processes;
   (c) an adaptively controlled equalizer, said equalizer electrically coupled to said accelerometers, said equalizer including means for generating equalizing signals which suppress intracranial vibration signals generated by said medical instrument;
   (d) an adaptive controller, said adaptive controller electrically coupled to said accelerometers and said equalizer, said adaptive controller including means for adapting said equalizing signals to changes in said intracranial vibration signals; and
   (e) transducing means for transmitting said equalizing signals to said patient.

6. An apparatus as recited in claim 5, further comprising means for calibrating said equalizing means.

7. An apparatus as recited in claim 5, wherein said transducing means comprises a vibrator configured for coupling to said patient.

8. A method for suppressing intracranial noise generated by a medical instrument, comprising the steps of:
   (a) sensing mechanical vibration signals generated by a medical instrument;
   (b) sensing, from a vibration sensor attached to the head of a patient, intracranial vibration signals induced by said medical instrument in the patient;
   (c) processing said mechanical and intracranial vibration signals and generating equalizing vibration signals which suppress said intracranial vibration signals;
   (d) adapting said equalizing vibration signals to changes in said mechanical and intracranial vibration signals; and
   (e) transmitting said equalizing vibration signals through a vibrator attached to the head of said patient.

9. A method as recited in claim 8, further comprising the step of calibrating said equalizing vibration signals.

* * * * *